(12) United States Patent
Andersen et al.

(10) Patent No.: US 6,702,838 B1
(45) Date of Patent: Mar. 9, 2004

(54) METHOD OF TREATING HYPOTROPHIC SCARS ENLARGED PORES

(75) Inventors: Dan E. Andersen, Menlo Park, CA (US); Eric F. Bernstein, Wynnewood, PA (US)

(73) Assignee: Lumenis Inc., Santa Clara, CA (US)

( * ) Notice: Subject to any disclaimer, the term of this patent is extended or adjusted under 35 U.S.C. 154(b) by 9 days.

(21) Appl. No.: 09/663,987

(22) Filed: Sep. 18, 2000

(51) Int. Cl.[7] .............................................. A61N 5/067
(52) U.S. Cl. ............................ 607/89; 607/88; 607/100
(58) Field of Search .............................. 606/2, 3, 9, 10, 606/13–17; 607/88, 89, 90

(56) References Cited

U.S. PATENT DOCUMENTS

| | | | |
|---|---|---|---|
| 5,312,395 A | 5/1994 | Tan et al. | |
| 5,810,801 A | 9/1998 | Anderson et al. | 606/9 |
| 5,911,718 A | 6/1999 | Yarborough et al. | |
| 5,938,657 A * | 8/1999 | Assa et al. | 606/11 |
| 5,964,749 A | 10/1999 | Eckhouse et al. | 606/9 |
| 5,983,900 A | 11/1999 | Clement et al. | 128/898 |
| 6,045,548 A | 4/2000 | Furumoto et al. | 606/9 |
| 6,077,294 A | 6/2000 | Cho et al. | |
| 6,235,016 B1 * | 5/2001 | Stewart | 606/9 |
| 6,379,376 B1 * | 4/2002 | Lubart | 606/2 |

OTHER PUBLICATIONS

T.S. Alster et al., "Improvement of facial acne scars by the 585 nm flashlamp–pumped pulsed dye laser," *Journal of the American Academy of Dermatology*, vol. 35, No. 1, Jul. 1996, pp. 79–81.

J.L. Cisneros et al., "The Q–switched Neodymium (Nd): YAG Laser with Quadruple Frequency," *Dermatol. Surg.*, vol. 24, 1998, pp. 345–350.

T.S. Alster et al., "Treatment of Scars: A Review," *Annuals of Plastic Surgery*, vol. 39, No. 4, Oct. 1997, pp. 418–432.

* cited by examiner

*Primary Examiner*—Roy D. Gibson
(74) *Attorney, Agent, or Firm*—Eitan, Pearl, Latzer & Cohen Zedek, LLP

(57) ABSTRACT

Skin including hypotrophic scars is irradiated with laser radiation having a wavelength between about 525 and 550 nanometers. The irradiation is delivered at a fluence that stimulates wound healing responses without actually inflicting a wound. The wound healing properties promote growth of dermal extracellular matrix. Absorption properties of hemoglobin and melanin in the 525 to 550 nanometer wavelength range provide that wound healing response is concentrated close to upper regions of the skin and accordingly close to the location of the scars. The growth of dermal extracellular matrix "bulks-up" irradiated dermal tissue. This makes the depressions of hypertrophic scars shallower and less apparent. The method has also been observed to cause shrinkage of enlarged pores.

29 Claims, 2 Drawing Sheets

METHOD OF TREATING HYPOTROPHIC SCARS ENLARGED PORES

TECHNICAL FIELD OF THE INVENTION

The present invention relates in general to laser treatment of dermatological imperfections. The invention relates in particular to non-ablative laser treatment of hypotrophic scars and enlarged pores.

DISCUSSION OF BACKGROUND ART

The aesthetic treatment of abnormal dermatological conditions such as scars and pores has hitherto involved primarily the removal of tissue and subsequent wound healing to improve their appearance. Chemical peels, dermabrasion, and ablative laser skin resurfacing are used routinely for this purpose. However, all of these methods leave open wounds which must subsequently heal. Prior-art treatments and investigations of treatments have been concentrated primarily on raised, keloid, or hypertrophic scars. Treatment of dermatological imperfections such as hypotrophic or depressed scars, such as those that are a common residual feature following acne treatment, has received relatively little investigative attention. While such imperfections may not be considered as aesthetically unpleasant or inconvenient compared with raised scars, which can often be discolored or crusted, they are nonetheless dermatological imperfections. There is need for a method of improving the character of these imperfections without causing damage to peripheral tissue, and without leaving an open wound which must subsequently heal

SUMMARY OF THE INVENTION

The present invention is directed to a method for treating any one or both of depressed scars or enlarged pores in human skin. In one aspect, the method of the present invention comprises irradiating the skin to be treated with light (electromagnetic radiation) having a wavelength selected such that it is preferentially absorbed in a dermal region of the skin including a melanocyte layer of the epidermis and a region of superficial vasculature immediately below the melanocyte layer. The light is delivered at a fluence sufficient that the preferential absorption thereof stimulates a wound healing response in the dermal region without causing a wound. The wound healing response promotes growth of dermal extracellular matrix (ECM) in the upper dermal region. The growth of dermal ECM reduces the depth of the depressed scars and reduces the size of the enlarged pores.

Preferably, the light has a wavelength between about 525 and 550 nanometers (nm). The light may be delivered in the form of pulses thereof or as a continuous beam swept or scanned over an area of skin being treated.

In experimental treatments in accordance with the present invention, pulsed electromagnetic radiation having a wavelength of 532 nm, delivered by a frequency-doubled Nd:YAG laser was arranged to deliver a spot having a diameter of about 3 millimeters (mm). The pulse duration was about 2.0 milliseconds (ms). An average fluence of 7.5 Joules per square centimeter ($J/cm^2$) was used to treat twenty-four volunteer patients having dermatological defects including depressed (hypotrophic) facial scars and enlarged pores. There was on average a 65% improvement in the appearance hypotrophic scars, and a 50% improvement in the appearance of enlarged pores.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the invention.

DETAILED DESCRIPTION OF THE INVENTION

The method of the present invention relies on using laser radiation to stimulate the skin's wound healing responses. The laser radiation wavelength and the laser radiation fluence are selected such that the wound healing responses are stimulated without actually inflicting a wound. The wound healing responses promote growth or production of dermal ECM. The term "wound" here is meant to define an open wound, blister or any other effect which would be manifest in, or lead to, necrosis of tissue.

The biology of wound healing is a very complex process. Cytokines released by the vascular endothelial cells and epidermal keratinocytes are responsible for initiating the increased production of ECM. These elements lie in the uppermost regions of the skin. This ECM production process takes place in a series of interrelated steps via the resident cells of the dermis. By selecting a wavelength of laser radiation in a range between about 525 and 550 nm, the wound healing response is concentrated close to these upper regions of the skin, and accordingly close to the location of imperfections being treated.

The dermis is composed of cellular and extracellular constituents that interact with one another to form a highly ordered yet quite dynamic structure. Other than water, the major components of the ECM are collagen,elastic fibers, fibronectin, glycosaminoglycans, and proteoglycans. The stimulated growth of dermal ECM "bulks-up" the dermal tissue. This makes the depressions of hypertrophic scars shallower and less apparent, if not eliminating them altogether. The method has also been observed to cause shrinkage of enlarged pores.

The superficial vascular endothelium and the epidermal keratinocytes are stimulated by heating them with light that is well absorbed by both structures. This requires that the light be optimally absorbed in both melanin and in hemoglobin of the superficial vasculature.

Figure 1:
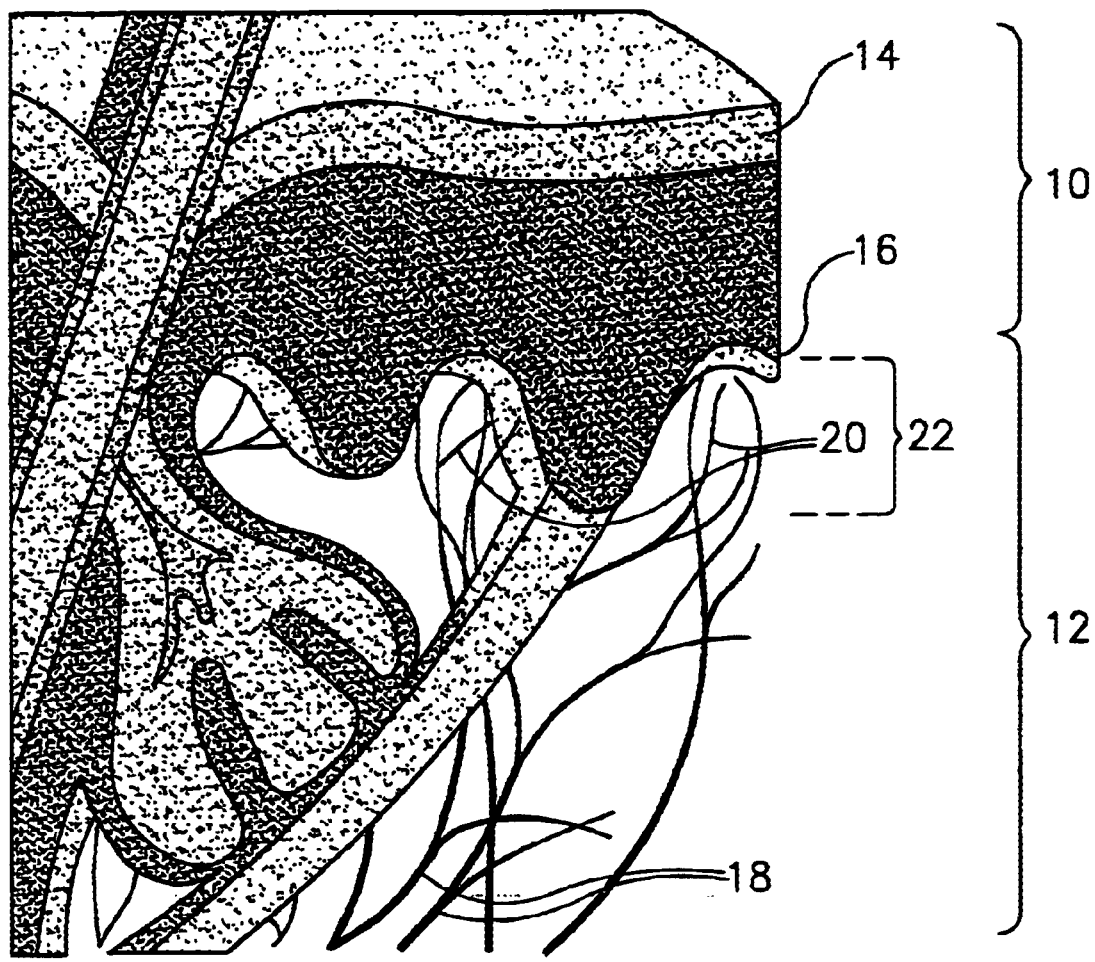
FIG. 1 schematically illustrates a section of human tissue including layers and vasculature thereof.

FIG. 1 schematically illustrates a section of human skin including a region 10 generally defined as the epidermis and a region 12 generally defined as the dermis. The epidermis 10 includes an outer layer (stratum corneum) 14, and a lower (melanocyte) layer 16 including melanin pigment. Some keratinocytes are heavily pigmented and contain melanosomes which feed melanin to surrounding cells. The epidermis is made up primarily of keratinocytes.

In the papillary or upper dermis 12, vasculature 18 has a superficial portion thereof comprising a plurality of capillary loops 20. In the method of the present invention, absorption by melanin in melanocyte layer 16 and hemoglobin in capillary loops 20 of vasculature 18 preferentially heats a shallow region 22 immediately below layer 16, thereby heating the layer by conduction and providing the desired wound healing stimulus. It is believed, without being limited to a particular theory, that heating of keratinocytes in the walls of vessels of vasculature 18, in particular of the capillary loops 20 close to the epidermis 10, induces the secretion of cytokines that stimulate cells of the dermis 12 to produce the ECM.

Figure 2:
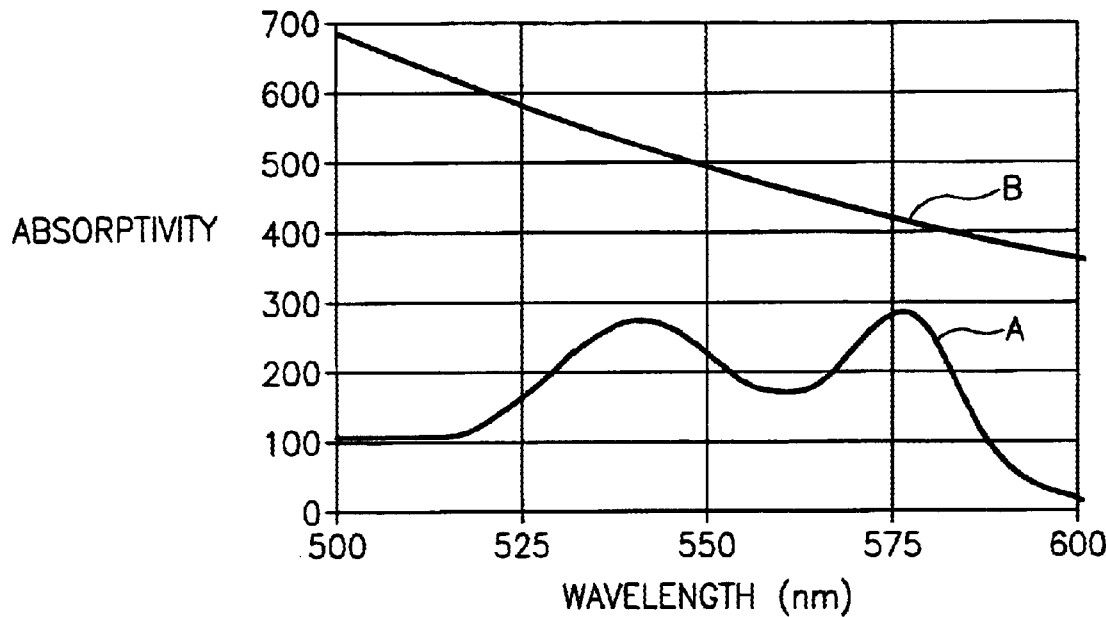
FIG. 2 is a graph schematically illustrating absorptivity of hemoglobin and melanin as a function of wavelength in a wavelength region of the visible electromagnetic spectrum between 500 nanometers and 600 nanometers.

FIG. 2 graphically, schematically illustrates absorptivity of blood (curve A) and melanin (curve B) as a function of wavelength in a wavelength region between 500 nm and 600 nm in the visible electromagnetic spectrum. In the preferred wavelength region of 525 to 550 nanometers absorptivity in haemoglobin is at or near a peak while absorption in melanin is also at a high level. The high melanosome absorptivity helps in maintaining the desired heating effect at the superficial level in skin being treated. By way of contrast, in the "yellow" wavelength region around 580 nm where dye lasers emit, melanosome absorptivity is significantly less than at 525 nm and approaches equality with hemoglobin absorptivity. This is one reason why dye lasers are preferred in prior-art treatment of vascular disorders and the like. In such treatments, absorption of radiation by melanin could cause undesirable side effects such as blistering of skin as well as preventing penetration of the radiation to the lower lying vasculature where it is needed.

In the inventive hypotrophic scar treatment method, electromagnetic radiation (light) preferably having a wavelength between about 525 and 550 nm, and having an appropriate pulse duration and intensity, is used to provide a selective, localized temperature increase in the superficial vasculature 20 and, intentionally and therapeutically, in melanocyte layer 16. The temperature rise should be sufficient to stimulate the release of cytokines and other growth factors without appreciably damaging any of the structures of the skin. Preferably this temperature is less than about 70° C., but must of, course, be higher than normal body temperature. It is believed that at wavelengths increasingly shorter than 525 nm, as absorption becomes increasingly, proportionately higher in melanin than in hemoglobin, that sufficient heating of the target region can not be obtained without overheating the melanocyte layer and causing blistering. At wavelengths increasingly longer than 550 nm, decreasing melanin absorption will allow penetration of radiation to depths in the vasculature at which it is less therapeutically effective, if at all.

The treatment radiation is preferably delivered by a laser. One suitable laser for providing radiation in the inventive treatment of hypotrophic scars and pores is a frequency doubled Nd:YAG laser. Such a laser operates most efficiently by generating 1064 nm fundamental radiation and converting this radiation to 532 nm radiation by intracavity frequency doubling.

Figure 3:
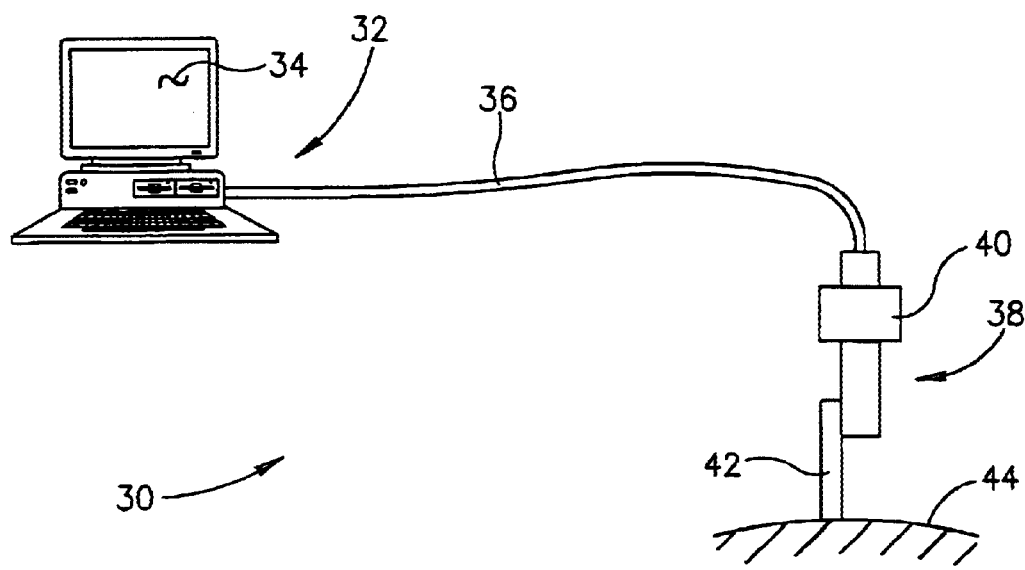
FIG. 3 schematically illustrates laser apparatus used for experimental treatment of hypotrophic scars and enlarged pores in accordance with the method of the present invention.

Referring now to FIG. 3, laser apparatus 30 used for experimental treatments in accordance with the present invention includes a Coherent® "VersaPulse V™" intracavity-frequency-doubled Nd:YAG laser 32 including a touch screen control display 34 for controlling operating parameters of the laser. Laser 32 delivers 532 nm radiation via a fiber-optic cable 36 to a handpiece 38. Handpiece 38 includes optics (not shown) which allow delivery of the 532 nm laser radiation focussed in a range of spot sizes. Spot sizes are selectively adjustable by rotating a control ring 40. A stand-off probe 42 attached to handpiece 38 contacts tissue 44 being treated to ensure that radiation is always delivered in the same spot size as the handpiece is moved to different locations on tissue 44. It is also possible to employ a handpiece that delivers a collimated beam. This allows for a range of variation of working distance while still maintaining a selected beam size.

In experimental treatments in accordance with the present invention, laser 22 was arranged to deliver a spot having a diameter of about 3 mm. The pulse duration was about 2.0 ms. An average fluence of 7.5 J/cm$^2$ was used to treat both depressed facial scars and enlarged pores of volunteer patients. A total of 24 volunteer patients were treated.

Scars having a size larger that 3.0 mm were treated by applying single pulses at adjacent locations over the area without overlapping pulses. There was a high degree of patient satisfaction with the improvement of their appearance after only two treatments (one treatment per month). There was on average a 65% improvement in hypotrophic scars and a 50% improvement of enlarged pores. The judgement of improvement being made by the patients themselves.

In establishing a suitable fluence for treatment for each patient, test pulses were delivered to a selected test area of that patient's skin, in a range of increasing fluences, until a fluence level was reached which produced observable inflammation. Each test pulse was fired on a different portion of the patient's skin. It was found that fluences higher than 12 J/cm$^2$ at a pulse length of 2 ms generally caused blistering, even on light-skinned patients. Accordingly a fluence less than about 10 J/cm$^2$ in a pulse having a duration of about 2 ms or less is preferred. It should be noted here that this simple inflammation does not constitute a wound as that term is defined herein. Under no circumstances should the fluence be sufficient to cause coagulation of blood in the vasculature.

Inflammation is a very specific process and is not synonymous with irritation. It is emphasized, however, that it is not necessarily the inflammation in itself that is responsible for the dermal ECM deposition and corresponding improvements of the inventive treatment. Rather, it is believed that it is the directed inflammatory process of the present invention which promotes the ECM growth, whether or not inflammation is clinically evident. Numerous inflammatory skin conditions, such as vasculitis, Sweet's syndrome and insect bites, occur without deposition of dermal ECM.

The experimental treatments were performed without resort to any skin cooling mechanisms such as contact cooling, cryogen spray cooling or the application of cooling gels to areas being treated. It is possible, however, that the method of the present invention may be made part of an integrated approach to the treatment of hypotrophic scars by combining the above-described radiation therapy with application of agents such as alpha-hydroxy acids, retinoids and growth factors that can positively impact the healing response.

It should be noted, here, that while the above-described experimental treatments were conducted using the 532 nm wavelength of a frequency-doubled Nd:YAG this particular wavelength should not be construed as limiting the invention. By way of example using an appropriately wavelength selective resonator, a frequency doubled Nd:YAG laser can be arranged to deliver other wavelengths in the region between about 525 nm and 555 nm. These other wavelengths are about 531 nm, about 537 nm and about 539 nm which can be produced by frequency doubling fundamentally radiation at respectively about 1061 nm, about 1073 nm and about 1078 nm, the term about here meaning that the wavelengths are stated as rounded to the nearest nanometer. 532 nm radiation may also be generated by a frequency-doubled Nd:YVO$_4$ laser. The use of any other laser providing radiation in the preferred, 525 nm to 550 nm range is not precluded in the present invention, nor is the use of any source of non-coherent light delivering radiation in this preferred wavelength range.

It should also be noted that while single pulse delivery of radiation in experimental treatments is described, it is also possible to use continuous wave (CW) radiation and scan the radiation over tissue being treated. Scan speed (accordingly the dwell time of a beam in a particular area) can be selected, consistent with the beam-size and power in the CW beam, such that the dwell time of radiation at a point being treated (due to the time taken for a beam of finite size to pass that point) delivers the appropriate fluence as indicated above.

The present invention is described above in terms of a preferred and other embodiments. The invention is not limited, however, by the embodiments described and depicted herein. Rather, the invention is limited only by the claims appended hereto.

What is claimed is:

1. A method for treating any one of hypotrophic scars and enlarged pores in human skin, comprising:
   irradiating the skin with light having a wavelength between about 525 nanometers and 550 nanometers at a fluence level sufficient to promote a wound healing response in the skin but insufficient to cause a wound.

2. The method of claim 1, wherein said wavelength is about 532 nanometers.

3. The method of claim 1, wherein said fluence is less than about 10 J/cm$^2$.

4. The method of claim 1, wherein said light is delivered in the form of one or more pulses.

5. The method of claim 4, wherein said one or more pulses each have a duration of about 2 milliseconds or less.

6. The method of claim 1, wherein said light is delivered as CW radiation and is scanned over an area of skin being treated.

7. The method of claim 1, wherein said light is coherent light delivered by a laser.

8. The method of claim 1, wherein said light is incoherent light.

9. The method of claim 1, wherein said light is absorbed preferentially in a region of skin including a melanocyte layer of the epidermis and a region of superficial vasculature immediately below said melanocyte layer, thereby heating said region of skin to a temperature higher than normal body temperature but less than about 70° C., said heating promoting said wound healing response.

10. A method for treating depressed scars in human skin, comprising:
    irradiating the skin with light having a wavelength between about 525 nanometers and 550 nanometers such that a region of the skin including a melanocyte layer of the epidermis and a region of superficial vasculature immediately below said melanocyte layer are heated to a temperature higher than normal body temperature but less than about 70° C., said heating stimulating the production of dermal extracellular matrix in said region of the skin, said dermal extracellular matrix production reducing the depth of said depressed scars.

11. The method of claim 10, wherein said wavelength is about 532 nanometers.

12. The method of claim 10, wherein the fluence of said light is less than about 10 J/cm$^2$.

13. The method of claim 10, wherein said light is delivered in the form of one or more individual pulses.

14. The method of claim 13, wherein said one or more pulses each have a duration of about 2 milliseconds or less.

15. The method of claim 10, wherein said light is delivered as CW radiation and is scanned over an area of skin being treated.

16. The method of claim 10, wherein said light is coherent light delivered by a laser.

17. The method of claim 10, wherein said light is incoherent light.

18. A method for treating enlarged pores in human skin, comprising:
    irradiating the skin with light having a wavelength between about 525 nanometers and 550 nanometers such that a dermal region including a melanocyte layer of the epidermis and a region of superficial vasculature immediately below said melanocyte layer are heated to a temperature less than about 70° C., thereby stimulating the production of dermal extracellular matrix in said dermal region, said dermal extracellular matrix production reducing the size of said enlarged pores.

19. The method of claim 18, wherein said wavelength is about 532 nanometers.

20. The method of claim 18, wherein the fluence of said light is less than about 10 J/cm$^2$.

21. The method of claim 18, wherein said light is delivered in the form of one or more individual pulses.

22. The method of claim 21, wherein said one or more pulses each have a duration of about 2 milliseconds or less.

23. The method of claim 18, wherein said light is delivered as CW radiation and is scanned over an area of skin being treated.

24. The method of claim 18, wherein said light is coherent light delivered by a laser.

25. The method of claim 18, wherein said light is incoherent light.

26. A method for treating depressed scars in human skin, comprising:
    irradiating the skin with light having a wavelength between about 525 nanometers and 550 nanometers such that it is preferentially absorbed in a region of the skin including a melanocyte layer of the epidermis and a region of superficial vasculature below said melanocyte layer, said light being delivered at a fluence sufficient that said preferential absorption thereof stimulates a wound healing response in said region of the skin without causing a wound, said wound healing response promoting growth of a dermal extracellular matrix in said region of the skin, thereby reducing the depth of said depressed scars.

27. The method of claim 26, wherein preferential absorption heats said dermal region to a temperature higher than normal body temperature but less than about 70° C., said heating stimulating said wound healing response.

28. A method for treating enlarged pores in human skin, comprising:
    irradiating the skin with light having a wavelength between about 525 nanometers and 550 nanometers such that it is preferentially absorbed in a region of the skin including a melanocyte layer of the epidermis and a region of superficial vasculature immediately below said melanocyte layer, said light being delivered at a fluence sufficient that said preferential absorption thereof stimulates a wound healing response in said dermal region without causing a wound, said wound healing response promoting growth of dermal extracellular matrix in said region of the skin, thereby reducing the size of said enlarged pores.

29. The method of claim 28, wherein preferential absorption heats said dermal region to a temperature higher than normal body temperature but less than about 70° C., said heating stimulating said wound healing response.

* * * * *